United States Patent [19]

Kilmer et al.

[11] Patent Number: 5,591,185

[45] Date of Patent: Jan. 7, 1997

[54] METHOD AND APPARATUS FOR REPROFILING OR SMOOTHING THE ANTERIOR OR STROMAL CORNEA BY SCRAPING

[75] Inventors: Lauren G. Kilmer, Tulsa; Robert E. Nordquist, Oklahoma City, both of Okla.; Michael Nadalsky, Redondo Beach; David R. Gibson, Lake Forest, both of Calif.

[73] Assignee: Corneal Contouring Development L.L.C., Tulsa, Okla.

[21] Appl. No.: 345,245

[22] Filed: Nov. 28, 1994

Related U.S. Application Data

[63] Continuation-in-part of Ser. No. 170,679, Dec. 20, 1993, Pat. No. 5,368,604, which is a continuation of Ser. No. 939,856, Sep. 2, 1992, abandoned, which is a continuation of Ser. No. 894,162, Jun. 3, 1992, abandoned, which is a continuation of Ser. No. 592,601, Oct. 4, 1990, abandoned, which is a continuation-in-part of Ser. No. 450,672, Dec. 14, 1989, Pat. No. 5,063,942.

[51] Int. Cl.⁶ .................................................. A61F 9/00
[52] U.S. Cl. ........................ 606/166; 606/161; 606/180
[58] Field of Search .................................. 606/166, 161, 606/5, 180

[56] References Cited

U.S. PATENT DOCUMENTS

| | | | |
|---|---|---|---|
| 2,249,906 | 5/1941 | Longoria | 128/305 |
| 2,480,737 | 3/1949 | Jayle | 128/305 |
| 3,074,407 | 1/1963 | Moon et al. | 606/166 |
| 3,172,404 | 3/1965 | Copenhaver | 128/2.1 |
| 3,797,921 | 3/1974 | Kilmer et al. | 351/7 |
| 3,976,077 | 8/1976 | Kerfoot, Jr. | 128/305 |
| 4,173,980 | 8/1979 | Curtin | 606/166 |
| 4,381,007 | 7/1983 | Doss | 128/303 |
| 4,423,728 | 1/1984 | Lieberman | 128/310 |
| 4,490,022 | 12/1984 | Reynolds | 351/211 |
| 4,526,171 | 7/1985 | Schachar | 128/305 |
| 4,619,295 | 10/1986 | Graybill | 128/305 |
| 4,665,913 | 5/1987 | L'Esperance | 128/303 |
| 4,665,914 | 5/1987 | Tanne | 128/305 |
| 4,688,570 | 8/1987 | Kramer et al. | 128/305 |
| 4,718,418 | 1/1988 | L'Esperance | 128/303.1 |
| 4,724,522 | 1/1988 | Belgrorod | 364/415 |
| 4,729,372 | 3/1988 | L'Esperance | 128/303.1 |
| 4,744,362 | 5/1988 | Grundler | 128/305 |
| 4,750,491 | 6/1988 | Kaufman | 128/305 |

(List continued on next page.)

FOREIGN PATENT DOCUMENTS

| | | | |
|---|---|---|---|
| 0208950 | 1/1987 | European Pat. Off. | |
| 0248569 | 12/1987 | European Pat. Off. | A61F 9/00 |
| 303174 | 2/1989 | European Pat. Off. | 606/166 |
| 2595243 | 9/1987 | France | 606/166 |
| 3433581 | 3/1986 | Germany | 606/166 |
| 3707004 | 9/1988 | Germany. | |

OTHER PUBLICATIONS

Barraquer, Joaquin; Ruillan, Joaquin, Microsurgery of the Cornea, Ediciones Scriba, Barcelona, S.A., 1984, pp. 50, 61, and 155.

Mueller et al., "Some Experiments on Corneal Grinding", Expil Eye Res. (1967) 6, 42–47, pp. 42–50.

Straatsma et al., "Stereotaxic Intraocular Surgery", Arch Ophthal, vol. 88, Sep., 1972, pp. 325–329.

Hiroshi Uozato, Ph.D., and David L. Guyton, M.D., Centering Corneal Surgical Procedures, American Journal Of Ophthalmology, Mar. 1987 pp. 264–275.

(List continued on next page.)

Primary Examiner—Michael H. Thaler
Attorney, Agent, or Firm—Head, Johnson & Kachigian

[57] ABSTRACT

A method for reprofiling or otherwise smoothing and enhancing the anterior or stromal cornea by scraping. The method is useful as a primary technique for reprofiling the stromal portion of the cornea following a lamellar keratectomy or as a secondary technique for use in combination with other corneal refractive procedure to dislocate debris and smooth and enhance a worked area of the cornea.

25 Claims, 9 Drawing Sheets

U.S. PATENT DOCUMENTS

| | | | |
|---|---|---|---|
| 4,763,651 | 8/1988 | Kaufman | 128/310 |
| 4,770,172 | 9/1988 | L'Esperance | 128/303 |
| 4,796,623 | 1/1989 | Krasner et al. | 128/305 |
| 4,798,204 | 1/1989 | L'Esperance | 128/303 |
| 4,807,623 | 2/1989 | Lieberman . | |
| 4,834,748 | 5/1989 | McDonald | 623/5 |
| 4,838,266 | 6/1989 | Koziol | 128/303.1 |
| 4,840,175 | 6/1989 | Peyman | 128/303.1 |
| 4,903,695 | 2/1990 | Warner et al. . | |
| 4,947,871 | 8/1990 | Grieshaber | 128/898 |
| 4,997,437 | 3/1991 | Grieshaber | 606/166 |
| 5,063,942 | 11/1991 | Kilmer et al. . | |
| 5,215,104 | 6/1993 | Steinert | 606/166 X |
| 5,269,795 | 12/1993 | Arnott | 606/166 |
| 5,318,044 | 6/1994 | Kilmer et al. . | |
| 5,368,604 | 11/1994 | Kilmer et al. . | |
| 5,395,385 | 3/1995 | Kilmer et al. . | |

OTHER PUBLICATIONS

Stephen F. Brint, M.D., D. Michael Ostrick, O.D., Coni Fisher, M.S., C.O.T., Stephen G. Slade, M.D., Robert K. Maloney, M.D., Robert Epstein, M.D., R. Doyle Stulting, M.D.., Ph.D., Keith P. Thompson, M.D., Six–Month Results of the Multicenter Phase I Study of Excimer Laser Myopic Keratomileusis, J. Cataract Refract Surg. vol. 20, Nov. 1994, pp. 610–615.

Douglas R. Wilson, M.D. and Arthur H. Keeney, M.D., D. Sc., Diagnostic and Surgical Techniques, Corrective Measures for Myopia, Survey of Ophthalmology, vol. 24, No. 4, Jan.–Feb. 1990, pp. 294–304.

Arturo Maldonado Bas, MD, Hugo Daniel Nano Jr. MD, In Situ Myopic Keratomileusis Results in 30 Eyes at 15 Months, Refractive & Corneal Surgery, vol. 7, May/Jun. 1991, pp. 223–231.

Ophthalmic Procedures Assessment Keratophakia and Keratomileusis: Safety and Effectiveness, American Academy of Ophthalmology, pp. 1332–1341.

Charles W. Flowers, Jr., M.D., and Peter J. McDonnell, M.D., Mechanical Methods in Refractive Corneal Surgery, University of Southern California School of Medicine, 1994 Current Science pp. 81–89.

Robert Haimovici, M.D., William W. Culbertson, M.D., Optical Lamellar Keratoplasty Using the Barraquer Microkeratome, Refractive & Corneal Surgery, vol. 7, Jan./Feb. 1991.

Khalil D. Hanna, M.D., Thierry David, M.D., Jeanine Besson, M.D., Yves Pouliquen, M.D., Lamellar Keratoplasty With the Barraquer Microkeratome, Refractive and Corneal Surgery, vol. 7 Mar./Apr. 1991 pp. 177–181.

Eduardo Arenas–Archila, M.D., Juan Camilo Sanchez–Thorin, M.D., Juan Pablo Naranjo–Uribe, M.D., Angel Hernandez–Lozano, M.D., Myopic Keratomileusis in Situ: A Preliminary Report, J. Cataract Refract Surg. vol. 17, Jul. 1991, pp. 424–435.

Waring III, M.D., F.A.C.S., George O., *Refractive Keratotomy for Myopia and Astigmatism, Optics and Topography of Radial Keratotomy*, Chapter 3 (pp. 37–139); *Centering Corneal Surgical Procedures*, Chapter 16 (pp. 491–505); and *Laser Corneal Surgery*, Chapter 19 (pp. 669–745). Mosby Year Book, Inc. 1992.

METHOD AND APPARATUS FOR REPROFILING OR SMOOTHING THE ANTERIOR OR STROMAL CORNEA BY SCRAPING

RELATED APPLICATIONS

This application is a continuation-in-part (CIP) of application Ser. No. 08/170,679, filed Dec. 20, 1993, now U.S. Pat. No. 5,368,604, which is a continuation of Ser. No. 07/939,856 filed Sep. 2, 1992, now abandoned, which is a continuation of Ser. No. 07/894,162 filed Jun. 3, 1992, now abandoned, which is a continuation of Ser. No. 07/592,601 filed Oct. 4, 1990, now abandoned, which is a continuation-in-part of Ser. No. 07/450,672 filed Dec. 14, 1989, now U.S. Pat. No. 5,063,942.

BACKGROUND OF THE INVENTION

This invention relates to a method and apparatus for adjusting the shape of components of the eye and more particularly to making fixed changes in the corneal curvature to correct refractive error.

Deviations from the normal shape of the corneal surface produce errors of refraction in the visual process. The eye in a state of rest, without accommodation, focuses the image of distant objects exactly on the retina. Such an eye enjoys distinct vision for distant objects without effort. Any variation from this standard constitutes ametropia, a condition in which the eye at rest is unable to focus the image of a distant object on the retina. Hyperopia is an error of refraction in which, with the eye at rest, parallel rays from distant objects are brought to focus behind the retina. Divergent rays from near objects are focused still further back. In one aspect of hyperopia, the corneal surface is flattened which decreases the angle of refraction of rays as they pass through the refractive surfaces of the cornea, causing a convergence or focus of the rays at a point behind the retina. The retina is comprised partially of nerve fibers which are an expansion of the optic nerve. Waves of light falling on the retina are converted into nerve impulses and carried by the optic nerve to the brain to produce the sensation of light. To focus parallel rays on the retina, the hyperopic eye must either accommodate, i.e., increase the convexity of its lens, or a convex lens of sufficient strength to focus rays on the retina must be placed before the eye. Myopia (Gr. to squint) is that refractive condition in which, with accommodation completely relaxed, parallel rays are brought to focus in front of the retina. One condition which commonly causes myopia is when the corneal curvature is steepened, thus the refraction of rays is greater as the rays pass through the refractive surfaces of the cornea, and the over-refracted rays converge or focus in front of the retina in the vitreous of the eye. When the rays reach the retina they become divergent, forming a circle of diffusion and consequently a blurred image. A concave lens is used to correct the focus of the eye for myopia.

The normal treatment of these classic forms of refractive error of the eye is with the use of eyeglasses or contact lenses, both of which have well-known disadvantages to the user. It has been estimated that 60 million pairs of eyeglasses and 3 million pairs of contact lens are sold annually.

Recent research has been directed to operative techniques to change the refractive condition of the eye. Radial keratotomy (RK) is by far the most commonly used keratorefractive procedure to correct myopia. RK involves making equally spaced radial incisions in the peripheral cornea around a 3.0 to 5.0 mm diameter central, uncut clear zone. These incisions weaken the paracentral and peripheral cornea, which under the influence of intraocular pressure, causes outward bowing of the peripheral cornea, a compensatory flattening of the central cornea. This central corneal flattening then leads to a reduction in myopia. Many factors have been identified that affect the outcome of the RK procedure which the predictability is significantly less than achieved with eyeglasses and contact lens. See *Mechanical Methods in Refractive Corneal Surgery,* Flowers, Jr. and McDonnell, *Current Opinions in Ophthalmology,* 1994, 5; IV:81–89. Refinements in RK, and alternatives thereto, continue to evolve. Such techniques are generally referred to as "keratorefractive techniques". Two such techniques are more particularly called keratophakia and keratomileusis. Keratomileusis involves the regrinding of a corneal lamella into a meniscus or hyperopic lens to correct myopia or hyperopia. A corneal optical cryolathe has been especially developed for this procedure and is also used in the keratophakia procedure, when a homograft ground into a convex lens is placed interlamellarly to correct aphakic hypermetropia. The homograft tissue (corneal lamella) is frozen with carbon dioxide. The homograft is cut by the lathe as a contact lens would be, i.e., to the optical power required to effect the desired optical correction of the cornea. In keratomileusis, the anterior corneal lamella is shaped by the lathe. Further evaluation and explanation of these procedures can be found in the American Academy Ophthalmology, Ophthalmic Procedures Assessment Committee report approved Feb. 15, 1992, entitled: *Keratophakia and Keratomileusis: Safety and Effectiveness.* Another form of correction called "myopic keratomileusis in situ" is widely reported. See *J Catatact Refrat. Surg.,* Vol. 17, July 1991, pages 424–435, Arena-Archila, et al. *Myopic keratomileusis in situ: A preliminary report.* Instead of modifying the stromal side of the resected disc (corneal lamella), the correction is made in the stromal bed. It is thus seen that present procedures in keratorefractive techniques are best limited to situations where other more standard corrective practices are found ineffective. It is readily seen that the limiting factors in such surgical techniques is the gross complexity involved not only with multiple incisions in corneal tissue for affecting the procedures but also complex suturing patterns, resulting in gross restructuring of the eye. The eye is thus faced with a difficult job of adjusting to this trauma.

Over the past few years developments have been made in the use of lasers as a means to reshape the cornea in an attempt to get rid of refractive errors. In these processes, pulsed lasers remove tissue from the cornea by shaving off or vaporizing portions of the corneal surface to cause it to flatten. The most common type is an Eximer laser. The fundamental effect of such a laser on tissue is a photochemical one, the breaking of molecular bonds with so much energy that the tissue fragments fly from the surface at supersonic speeds, leaving behind a discreet space. The process has been designated as ablative photodecomposition or photoablation. Complete explanation of "laser therapeutic keratectomy" can be found in *Refractive Keratotoy,* George O. Waring III, Mosby year Book, (1992) Chapter 19. The laser techniques are adaptable to be used in other corneal surgical techniques, including keratomileusis in-situ.

One of the problems with keratomileusis procedures is obtaining a smooth curvature upon the exposed stromal bed. See *In Situ Myopic Keratomilesus Results in 30 Eyes at 15 Months,* Bas & Nano, *Refractive & Corneal Surgery,* Vol. 7, pages 223–231, May/June 1991. Using laser techniques leave corrugated or rippled ablated surfaces, like a washboard. In addition the ablated surface becomes 'work hardened' and contains a pseudo membrane of burned tissue that must be cleaned and cleared up.

As in all refractive correcting techniques, the risk benefit ratio is always considered individually and fully explained to prospective patients. See *Corrective Measures for Myopia*, Wilson and Keeney, *Survey of Ohthalmology*, Vol. 34, No. 4, Jan/Feb 1990, pages 294–304.

SUMMARY OF THE INVENTION

It is therefore an object of the present invention to provide a new and improved keratorefractive technique involving method and apparatus for changing the shape of the optical zone of the cornea to correct refractive errors of hyperopia (far-sightedness), myopia (near-sightedness), and astigmatism, whereby a non-spherical surface exists on the eye system and the simplicity of the technique virtually eliminates the chance of error or further complications resulting from gross disturbances of the eye system.

With this and other objects in view, the present invention contemplates a method and apparatus that can be variously described as ablating, scarifying, scraping, sculpting, or removing portions of the cornea for the purposes of correcting refractive error in human cornea. For the purposes of this invention, the apparatus and methods are applicable to correcting the cornea not only to the anterior surface, but also for use in keratomileusis and laser therapeutic keratectomy, including keratomileusis in-situ procedures.

Another object of the invention is to provide mechanical apparatus capable of easily being used by a surgeon for scraping the cornea in order to correct refractive errors of hyperopia, myopia, and astigmatism which includes means to provide consistency in depth and configuration of the surface.

Another object of this invention is to provide method and apparatus for scraping the cornea wherein the cornea is maintained in a more rigid posture during the procedure to eliminate flexure of the cornea and thus provide greater accuracy in determining predicable amounts of corneal material to be removed. This is accomplished by creating a vacuum not only as a means to establish the fixation of the apparatus upon the eye, but also in the operative space above the cornea during the process.

Specifically, the method objects of this invention involve the surgical reprofiling of the corneal portion of an eye of humans, to change the corneal radius and thus correct refractive errors. The preliminary clinical evaluation steps are well known to the practicing surgeon of the art. That is, the refractive power of the patient's eye is determined from the power of the cornea, the depth of the anterior chamber, the power of the lens, and the axial length of the globe. Of primary concern is the shape of the corneal surface and measurements are made to determine the radius of curvature, the central thickness, central anterior and posterior radius, the peripheral thickness and refractive index. Instruments used are described in *Refractive Keratotomy, supra*, in Chapter 3. The steps typically include creating a placido ring keratograph of a simulated cornea having the correct refractive qualities. Next, an actual keratograph of the cornea is created. The two kerotographs are compared to determine the amount of refractive error, i.e. whether it would be hyperopia, myopia, or astigmatism.

A reprofiling tool is constructed to include a plurality of scraper blades of shape sufficient to change a corneal radius to that of the simulated cornea. The reprofiling tool is then positioned within a holding sleeve that is contiguously positioned upon a vacuum fixation ring held on the eye such that the scraper blades will contact the cornea. A vacuum can also be used in the chamber above the cornea wherein the scraping tool is positioned. The scraping tool is then rotated or oscillated either by hand or motorized with the axial movement of the scraping tool being changed and indexed until the corneal radius has been corrected to that of the simulated or ideal cornea.

The apparatus used to achieve the objects of this invention specifically include a cylindrical fixation/adaptor sleeve assembly having a resilient and transparent vacuum ring means on its bottom side for temporary attachment to the sclera portion of an eye which surrounds the cornea that is to be reprofiled. A micrometer assembly, which holds the surgical knife in place is positioned upon the fixation ring/adaptor/sleeve assembly by the shoulder of a nut assuring proper translation alignment. An optical viewer positioned along the optical axis includes a camera and connected video monitor provides continual viewing of the ablation process. Illumination of the cornea for the optical viewer is possible with the use of a fiberoptic bundle. The assembly is connected to a handle. In addition to the video monitor and an illumination source, a vacuum console provides instrumentation and control of vacuum to the fixation/sleeve assembly and to the space above the cornea as needed.

Although the anatomic zones of the cornea include a geometric center, apex, the pupillary axis, line of sight, the visual axis and optical axis, which axis to position the apparatus is subject to some conflicting definition. Whichever it may be for the purposes of this invention, it will be called the "visual axis". Further discussion can be found in *Refractive Keratotomy, supra* in Chapter 16.

DETAILED DESCRIPTION OF THE PREFERRED EMBODIMENT

Before explaining the present invention in detail, it is to be understood that the invention is not limited in its application to the details of the construction and arrangement of parts illustrated in the accompanying drawings. The invention is capable of other embodiments and of being practiced or carried out in a variety of ways. It is to be understood that the phraseology and terminology employed herein is for the purpose of description and not of limitation.

Figure 1:
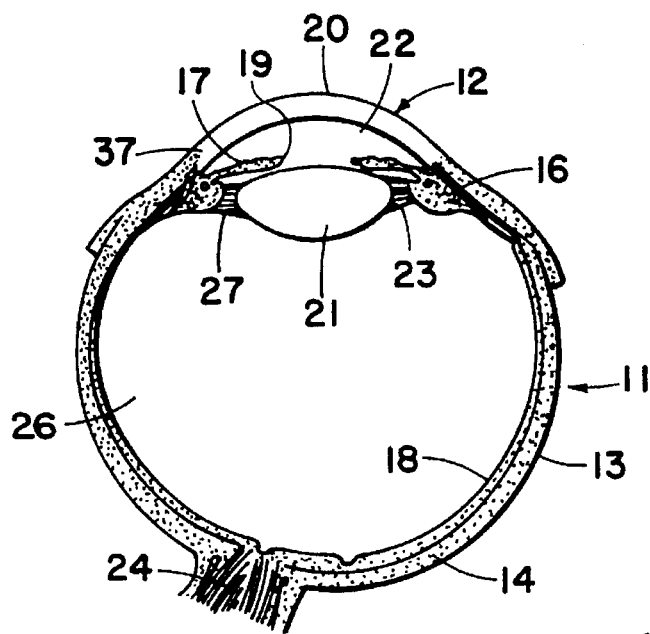
FIG. 1 is a schematic illustration of a horizontal section of the eye.

Referring first to FIG. 1 of the drawings, a horizontal section of the eye shows the globe of the eye resembling a sphere with an anterior bulged spherical portion 12 representing the cornea. Thus the eye is actually comprised of two somewhat modified spheres placed one in front of the other. The anterior of these two segments is the smaller more curved cornea.

The globe of the eye consists of three concentric coverings enclosing the various transparent media through which the light must pass before reaching the sensitive retina. The outermost covering is a fibrous protective portion, the posterior five-sixths of which is white and opaque and called the sclera 13, and sometimes referred to as the white of the eye where visible to the front. The anterior one-sixth of this outer layer is the transparent cornea 12.

A middle covering is mainly vascular and nutritive in function and is comprised of the choroid 14, ciliary body 15 and iris 17. The choroid generally functions to maintain the retina. The ciliary muscle is involved in suspending the lens and accommodation of the lens. The iris is the most anterior portion of the middle covering of the eye and is arranged in a frontal plane. It is a thin circular disc corresponding to the diaphragm of a camera, and is perforated near its center by a circular aperture called the pupil 19. The size of the pupil varies to regulate the amount of light which reaches the retina. It contracts also to accommodation, which serves to sharpen the focus by diminishing spherical aberration. The iris divides the space between the cornea 12 and the lens 21 into an anterior chamber 22 and posterior chamber 23. The innermost portion of covering is the retina 18, consisting of nerve elements which form the true receptive portion for visual impressions.

The retina is a part of the brain arising as an outgrowth from the fore-brain, with the optic nerve 24 serving as a fibre tract connecting the retina part of the brain with the fore-brain. A layer of rods and cones, lying just beneath a pigmented epithelium on the anterior wall of the retina, serve as visual cells or photoreceptors which transform physical energy (light) into nerve impulses.

The vitreous 26 is a transparent gelatinous mass which fills the posterior four-fifths of the globe. At its sides it supports the ciliary body 16 and the retina 18. A frontal saucer-shaped depression houses the lens 21.

The lens 21 of the eye is a transparent bi-convex body of crystalline appearance placed between the iris 17 and vitreous 26. Its axial diameter varies markedly with accommodation. A ciliary zonule 27, consisting of transparent fibers passing between the ciliary body 16 and lens 21 serves to hold the lens in position and enable the ciliary muscle to act on it.

Referring again to the cornea 12, this outermost fibrous transparent coating resembles a watch glass. Its curvature is somewhat greater than the rest of the globe and is ideally spherical in nature. However, often it is more curved in one meridian than another, giving rise to astigmatism. A central third of the cornea is called the optical zone with a slight flattening taking place outwardly thereof as the cornea thickens towards it periphery. Most of the refraction of the eye takes place on the surface of the cornea.

Figure 2:
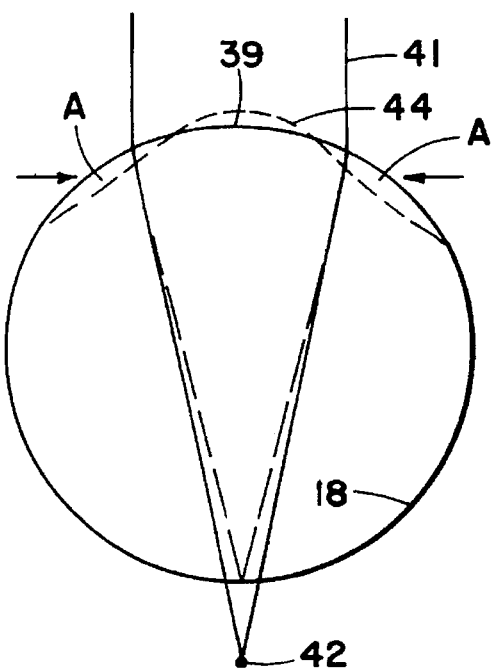
FIG. 2 is a schematic illustration of a hyperopic eye showing adjustment of the cornea to shorten the radius of curvature.

Referring next to FIG. 2 of the drawings, the globe of an eye is shown having a cornea 12 with a normal curvature represented by the solid line 39. If parallel rays of light 41 pass through the corneal surface 39 of FIG. 2, they are refracted by the corneal surfaces to converge eventually near the retina 18 of the eye. The diagram of FIG. 2 discounts, for the purposes of this discussion, the refractive effect of the lens or other portions of the eye. The eye depicted in FIG. 2 is hyperopic and thus the rays of light 41 are refracted to converge at point 42 behind the retina. If a peripheral band of pressure is applied inwardly at the chord 43 of the cornea, the walls of the cornea are caused to steepen. This is because the volume of fluids within the anterior chamber 22 remains constant, thus the anterior portion of the cornea, including the optical zone (inner third of the cornea) steepens in slope to form a curvature (shown in exaggeration) following the dotted line 44. The rays of light 41 are then refracted from the steeper surface 44 at a greater angle to direct the refracted rays into focus at shorter distance, such as directly on the retina 18.

Figure 3:
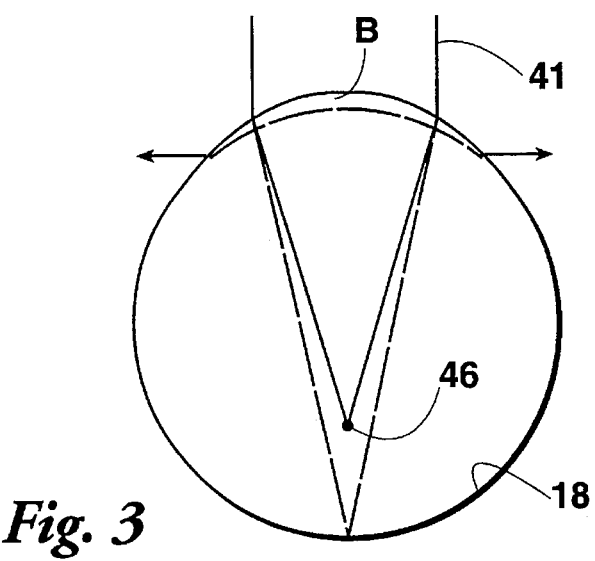
FIG. 3 is a schematic illustration of a myopic eye system showing adjustment of the cornea to increase its radius and thus flatten the corneal slope.

FIG. 3 shows a similar eye system to that of FIG. 2 except that the so-called normal corneal curvature of FIG. 3 causes the light rays 41 to refract into focus at a point 46 in the vitreous which is short of the retinal surface 18. This is typical of a myopic eye. If chord 43 of the cornea is expanded uniformly outwardly as shown by the arrows, the walls of the cornea are flattened. Light rays 41 refracted by the now-flattened corneal surface will be refracted at a smaller angle and thus converge at a more distant point such as directly on the retina 18.

Figure 4:
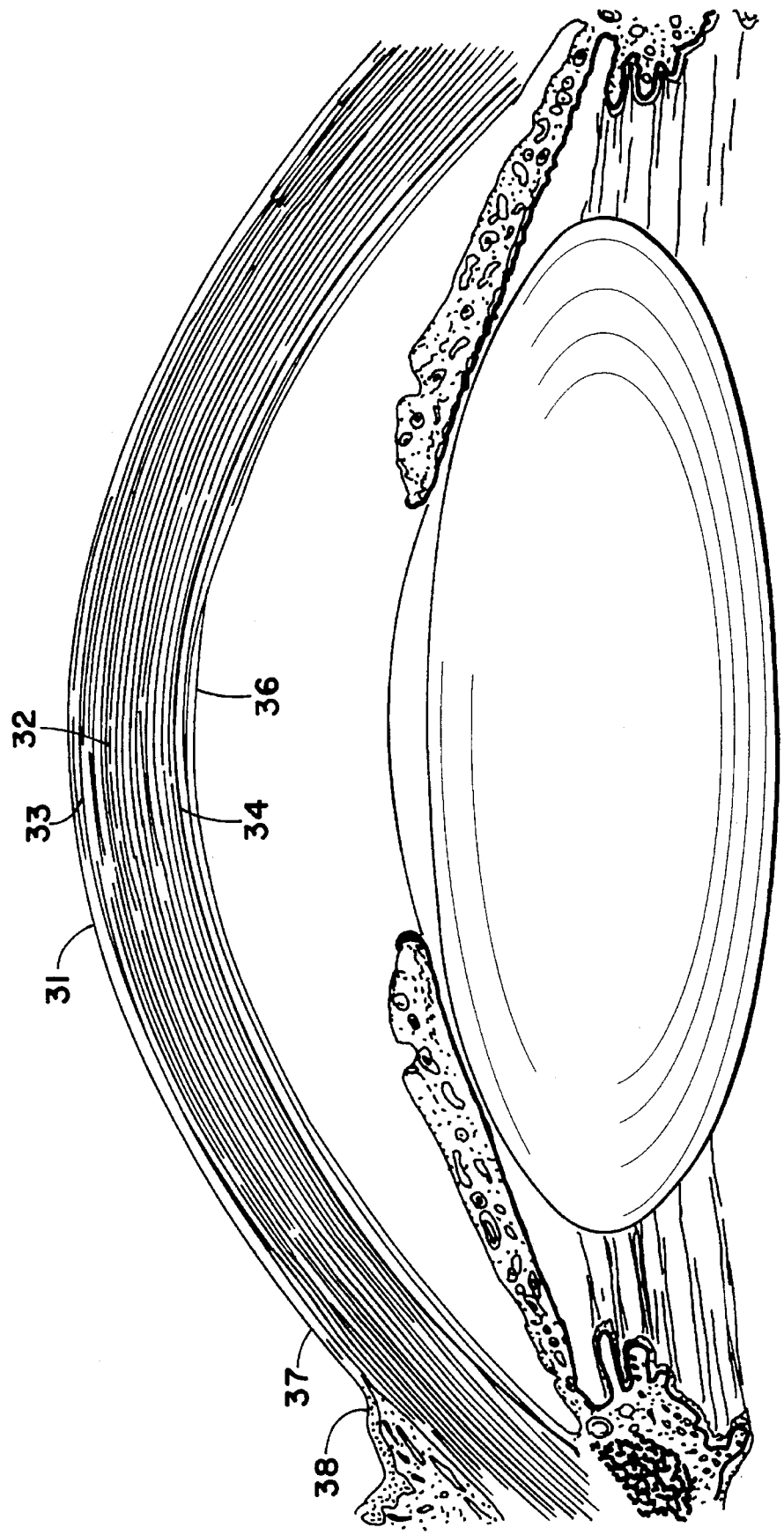
FIG. 4 is a detailed schematic illustration of a horizontal section of the frontal portion of an eye showing the various layers of the cornea.
Figure 5:
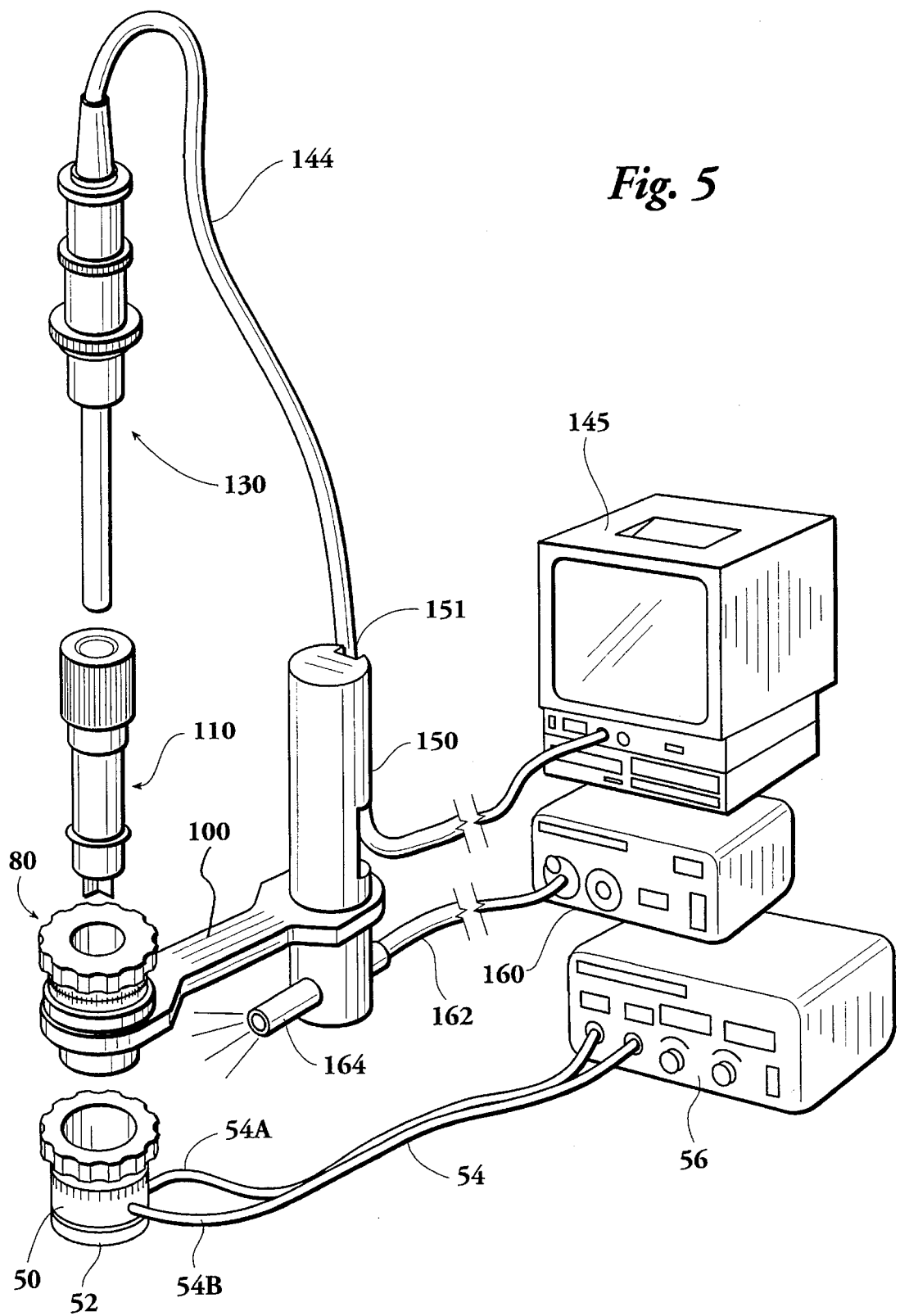
FIG. 5 is an exploded view showing the system components of the apparatus of this invention.
Figure 6:
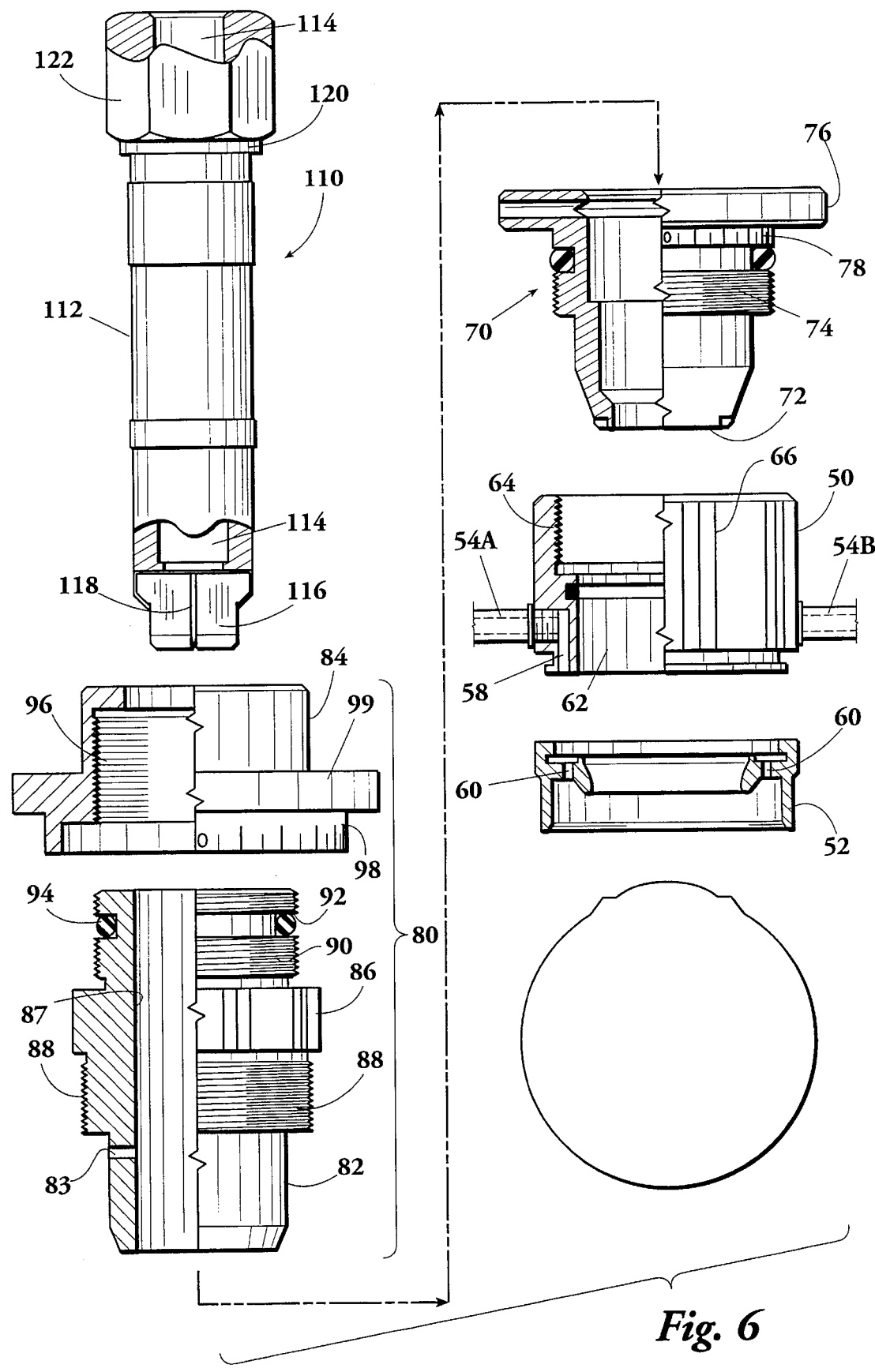
FIG. 6 is an exploded view of the various components of the basic apparatus for performing the ablation process of this invention.

Referring now to FIG. 4, a more detailed drawing of the anterior portion of the globe shows the various layers of the cornea comprising an epithelium 31. The cornea itself is 550 μm thick centrally, 700 μm peripherally, 12 mm diameter horizontally, and 11 mm diameter vertically. (Compare a credit card about 800 μm thick and a dime 13 mm in diameter.)

The epithelium is a five-to seven-layer (30 to 50 μm) which has three major functions:

1. Act as a mechanical barrier to foreign material and microorganisms,
2. Create a smooth, transparent optical surface for the tear film to adhere, and
3. Maintenance of a barrier to the diffusion of water solutes, and drugs.

Epithelial cells on the surface thereof function to maintain transparency of the cornea. These epithelial cells are rich in glycogen, enzymes and acetylcholine and their activity regulates the corneal corpuscles and controls the transport of water and electrolytes through the lamellae of the stroma 32 of the cornea.

An anterior limiting lamina 33, referred to as Bowman's membrane, is positioned between the epithelium 31 and the substantia propria or stroma 32 of the cornea. The stroma is comprised of lamella having bands of fibrils parallel to each other and crossing the whole of the cornea. While most of the fibrous bands are parallel to the surface, some are oblique, especially anteriorly. The fibrous bands within alternate lamella are at a near right angle to bands in the adjacent lamella. A posterior limiting lamina 34 is referred to as Descemet's membrane. It is a strong membrane sharply defined from the stroma and resistant to pathological processes of the cornea.

The endothelium 36 is the most posterior layer of the cornea and consists of a single layer of cells. The limbus 37 is the transition zone between the conjunctiva 38 and sclera 13 on the one hand and the cornea 12 on the other.

Figure 7:
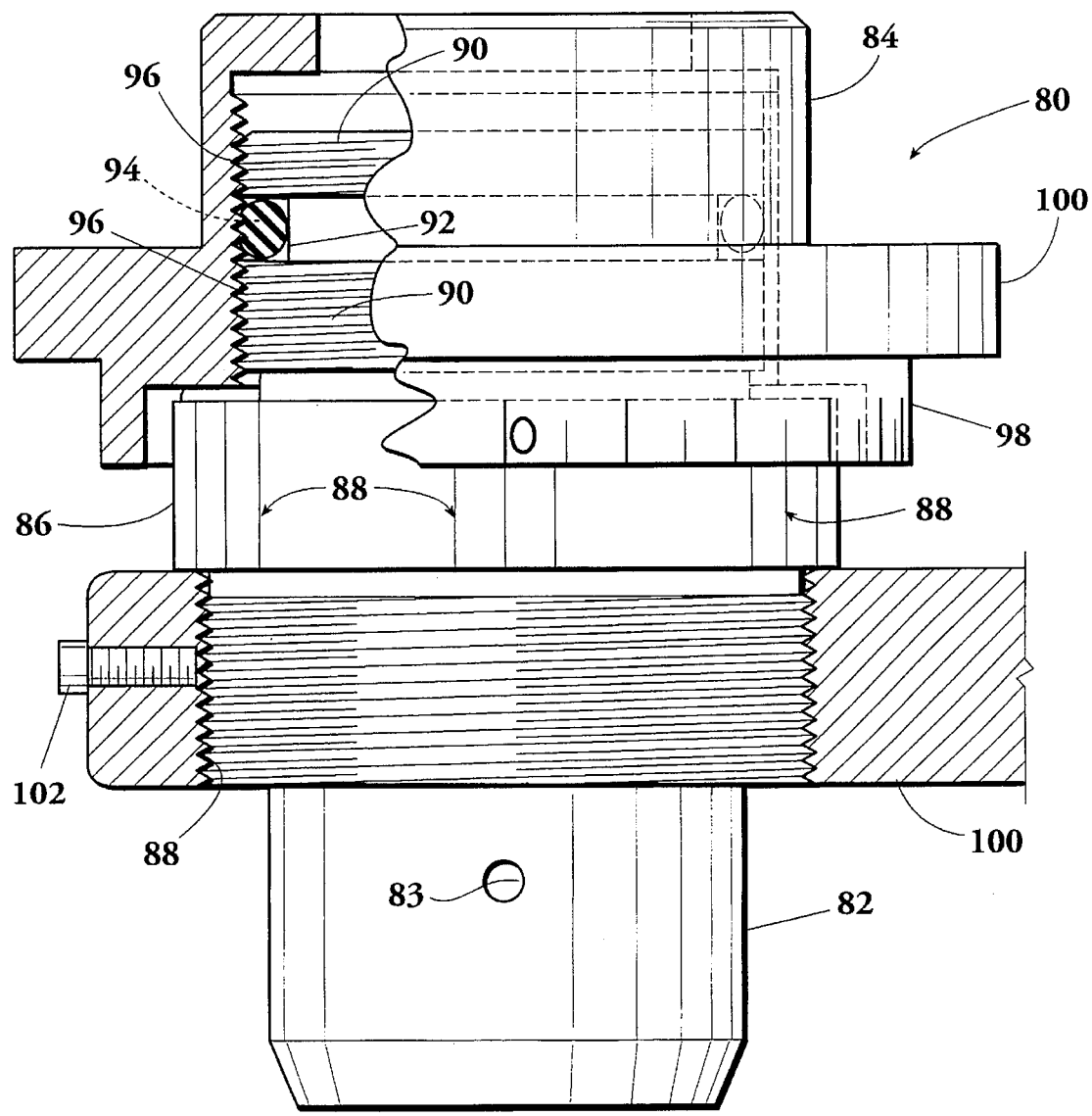
FIG. 7 is a partial sectional view of the fixation ring micrometer assembly of the invention.
Figure 8:
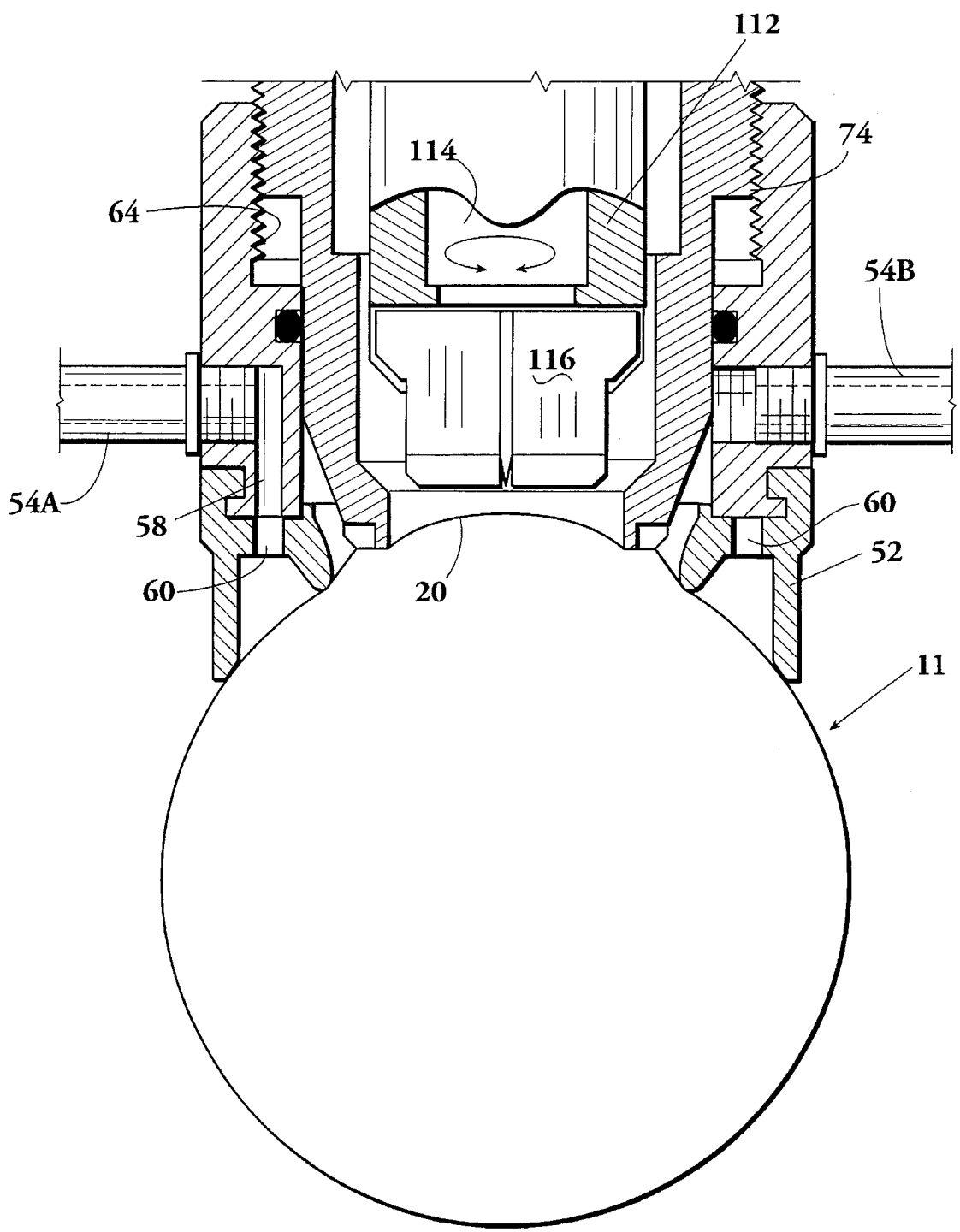
FIG. 8 is a partial sectional view of the lower portion of the assembly as placed upon the eye.
Figure 9:
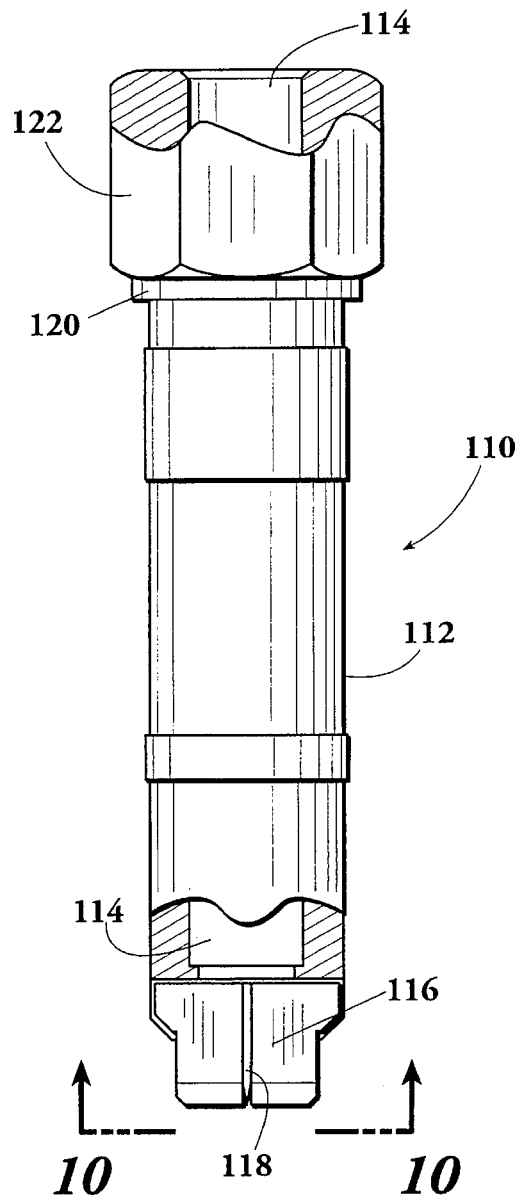
FIG. 9 is an elevational view of the knife assembly.
Figure 10:
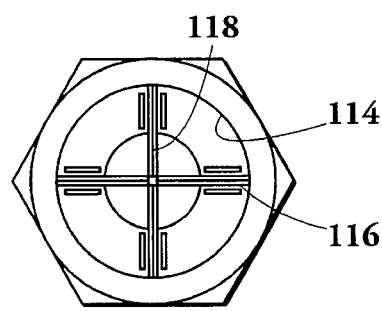
FIG. 10 is an end view of the knife assembly taken along the line 10–10 of FIG. 9.
Figure 11:
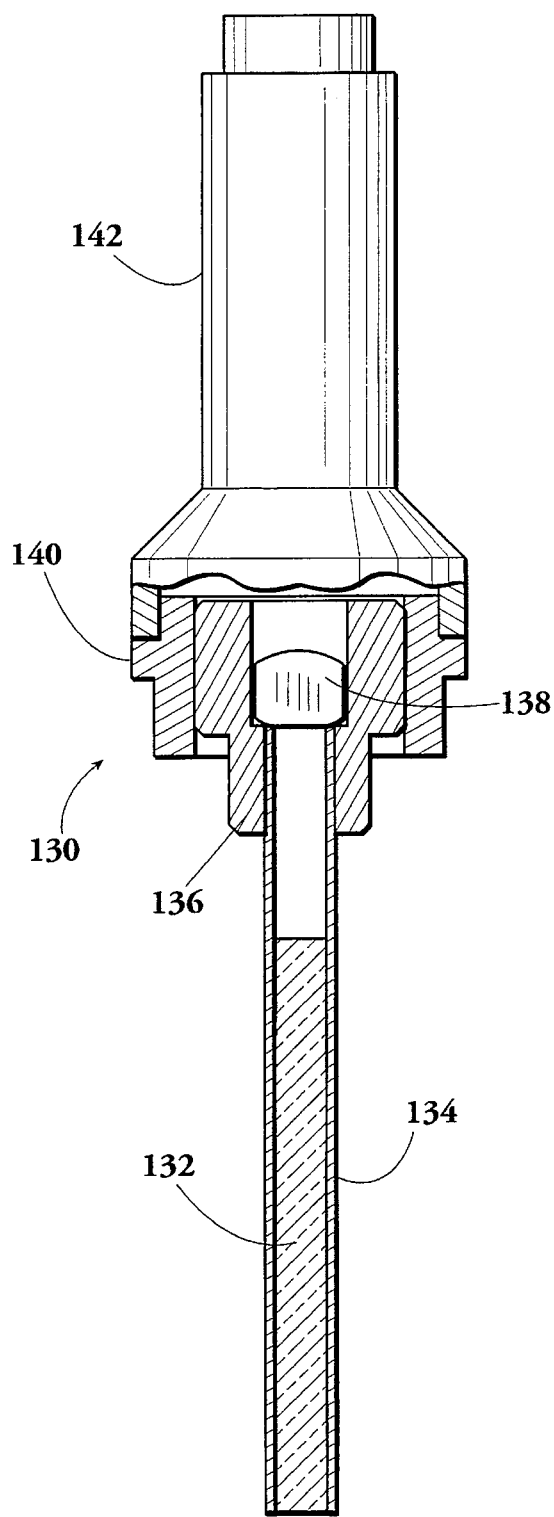
FIG. 11 is a partial sectional view of the optical viewer used with the apparatus of this invention.

Referring now to FIGS. 5–11, the assembly of the basic parts of the apparatus are shown in exploded and assembled views. These parts comprise a cylindrical fixation adapter and sleeve assembly ring 50 having a resilient vacuum ring 52 extending from the bottom side of the positioning ring for contact with the eye of the patient being treated. A vacuum hose 54 comprised of two hoses 54A and 54B provides communication between the inside of the resilient ring 52 and a controllable vacuum pump source and console means 56 to retain the assembled parts upon the eye for the surgical procedures herein described. Vacuum tube 54A connects with the fixation ring 50 and is in communication with the vacuum ring 52 by way of a plurality of conduits 58 in the fixation ring communicating with a plurality of conduits 60 in the resilient ring 52. Vacuum conduit 54B is in communication with the interior space 62 at the bottom of the fixation ring. The upper portion of the adapter 50 includes a plurality of micrometer-like threads 64, while the exterior of the adapter includes a plurality of vertical alignment indicia generally designated by the numeral 66. A positioning nut or sleeve is generally designated by the numeral 70 and comprises a reduced diameter lower tip 72. This tip is inwardly beveled so as to make surface contact with the cornea during the procedure as explained hereinafter. Micrometer threads 74 are adapted to engage with the threads 64 of the adapter 50. The upper portion of the sleeve terminates with a larger diameter knurled hand wheel 76 below which is a cylindrical micrometer indicia skirt 78 which are used for alignment with the indicia 66 of the adapter 50. The interior of the positioning sleeve includes openings to receive the surgical micrometer assembly, generally designated by the numeral 80, having lower body 82 and an upper body 84, the assemblage of which is best shown in FIG. 7. The lower body is retained within a horizontal support arm 100 by threads 88 or by any fastening means and held by a retention bolt 102. Above the support arm and formed as a part of the lower body is flange 86 which includes a plurality of indicia comprised of a series of spaced, vertical lines around the circumference. The remaining part of the lower body above the sleeve 86 includes a threaded portion 90, between which is an O-ring groove 92 and O-ring 94. The upper body 84 includes internal micrometer threads 96 which engage with threads 90. Exteriorly, is a skirt 98 and a hand wheel 99. The skirt 98 includes micrometer indicia which are used during the surgical procedure to adjust the surgical knife vertically relative to the cornea the desired amount. An opening 83 is found in the lower portion of the lower body to permit vacuum to enter the interior which will be above the cornea during the surgical procedure.

The surgical knife of this invention is generally designated by the numeral 110 as comprised of a vertical body 112 having an opening 114 therethrough. At the lower end of the surgical knife are plurality of transverse surgical blades 116 and 118. At the upper end is a sleeve 120 and a handle nut 122. The opening 114 is adapted to receive the optical viewer generally designated by the numeral 130. The diameter of the body 112 is adapted to slideably fit within the interior 87 of the micrometer assembly lower body 82.

The optical viewer 130 comprises a lens rod 132 which is filled with optical cement 134. The upper end of the lens rod is retained within a lens mount 136 which retains lens 138 as shown. A C-mount adaptor 140 is adapted to accept at its upper end the video camera 142 which in turn is connected to the TV monitor 145 through a flexible cable 144 which loops above the top of the camera and is contained within a cable groove 151 located in the back of handle 150. The optical assembly is inserted concentrically in the surgical knife assembly opening 114. The bottom end of the viewer system is adapted to be located just above the orthogonal knives and relays the corneal image to the other end of the viewer which then focuses the image upon the CCD camera 142. The handle support bracket 150 and its connection support 100 provide means to retain in axial alignment the micrometer assembly 80, optical viewer 130 and the fixation ring and adaptor sleeve assembly and provide means for the surgeon to handle and control the device. There is a groove in the bottom of the handle to accommodate a fiber optic illuminator cable 162 the output end of which is positioned contiguous to the fixation ring/adaptor sleeve assembly.

The console 56 connects to the fixation ring/adaptor sleeve assembly and provides vacuum supply by way of conduits 54A and 54B to the fixation ring and the adaptor sleeve assembly respectively. Two independent vacuum pumps and dedicated vacuum regulators comprise the working system of the console. The vacuum for each conduit is adjustable using regulators. Actual vacuum is read on analog gauges for each vacuum source and is documented with a chart recorder connected to vacuum pressure transducers that are contained within the console.

The fixation ring 52 is preferably made of silicone rubber that is designed to be placed over the eye contacting the sclera, and held there by vacuum ranging from 1–10 inches Hg (depending upon variations of corneal topography). The purpose of the fixation ring is to provide a means by which the corneal contouring system is positioned over the operative sight. The fixation ring is snapped onto the base of the adaptor sleeve assembly 50. The adaptor sleeve is typically made of polycarbonate and preferably transparent and provides a mounting for the micrometer assembly and for alignment of the assembled device with the cornea. The nut 70 is designed to be lowered onto the surface of the cornea in order to assist in holding it in place, i.e., prevent "corneal creep", during the procedure. The nut also connects to the vacuum line 54B which assists in stabilizing the cornea during the surgical procedure. The adaptor sleeve assembly also serves the function of allowing the transmission of light from source 164 onto the operative sight which is required when using the optical viewer system 130.

The micrometer assembly 80 consists of two parts: the micrometer body 82 (through the bore 87 of which the surgical knife passes) and the micrometer nut 84 (which is threaded onto the micrometer body). The micrometer assembly is retained to the support bracket 100 by threads 88. The bracket 100 connects with the tubular handle 150 and is locked in place there by a thumb screw. Rotating the micrometer nut adjusts the height of the top surface of the micrometer upon which the surgical knife 110 rests. The markings upon the micrometer nut and body represent 10 μm and provide a visual indication to the surgeon of the depth of movement. For example, a movement of one mark to an adjacent mark on the micrometer nut raises or lowers the micrometer 10 μm.

The surgical knife assembly 110 has two stainless steel sharpened blades permanently staked at 90° angles at the end of the surgical knife shaft. The proximal end of the shaft is hexagonally shaped turning knob 122 which can be knurled for ease and gripping. The turning knob is used to manually rotate the surgical knife blade. The knife blade assembly 110 fits into the bore of the micrometer assembly 80 and rests flatly on top of the micrometer nut 84. Thus, as the micrometer nut is rotated, the surgical nut assembly raises or lowers accordingly. The sharpened knife blades are substantially planar. The blades are oriented substantially perpendicular relative to the eye during the scraping procedure.

Figure 12:
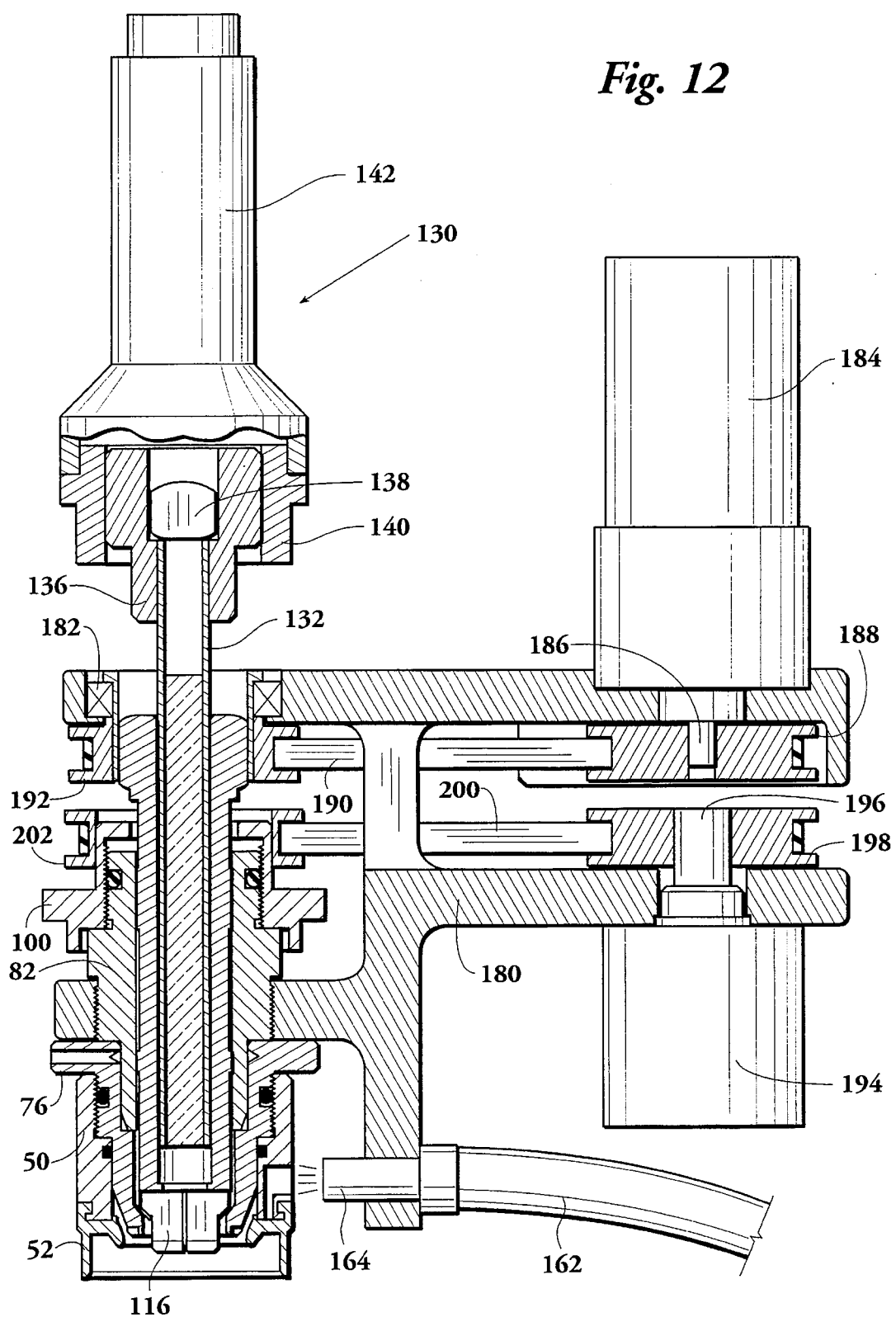
FIG. 12 is a partial sectional view of a motorized form of apparatus.

FIG. 12 represent a motorized version of the invention and comprises a support member 180 that is attached to an upper support 181 for the surgical assembly via bearing assembly 182 and at the lower end to the micrometer lower body 82. A first motor 184 has its output shaft 186 connected to pulley 188 driving a belt 190 which connects to the surgical knife body 112 which rests upon micrometer nut 202. A second potentiometer 194 has its output shaft 196 connected to a pulley 198 and belt 200 for driving the micrometer nut 202 for adjusting the vertical position of the surgical knife blade and body 204.

Figures 13A, 13B, 13C:
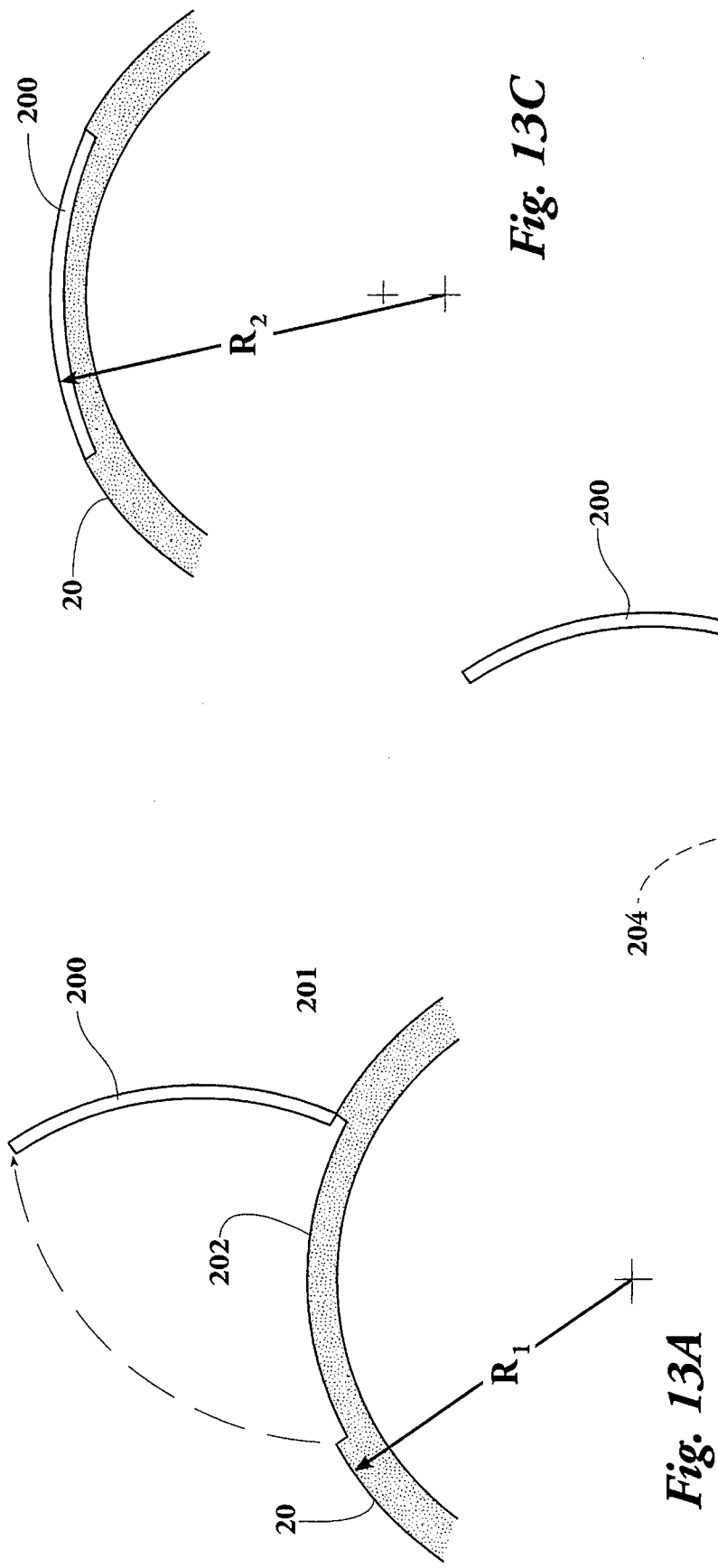
FIG. 13 (which includes FIGS. 13A, 13B and 13C) is a schematic of a keratomileusis procedure.

FIG. 13 is a schematic depiction of the process of keratomileusis in situ utilizing the concepts of this invention. In FIG. 13A lamellar keratectomy is performed upon cornea 20, having a given radius $R_1$ creating the resected disc 200 which, in a preferred arrangement, remains hinged to the cornea at one side at point 201, creating a stromal bed 202. The stromal bed is then modified, as for example, to correct for myopia, creating a flatter curve 204 (dotted) by the use, as for example, laser therapeutic keratectomy. In combination or in lieu thereof, the apparatus of this invention may be used to surgically scrape the stromal bed in a manner to achieve the desired curve.

The resected disc is then returned to contact with the stromal bed and sutured which is removed a few days thereafter. As a result, as for a myopic eye, the radius of curature $R_2$ is now greater. It is to be understood, however, that the process is also adaptable to correct hyperopia depending upon the reforming of the stromal bed 202.

The operation of the apparatus and the methods of surgery are accomplished by first taking optical measurements of the eye as to the shape of the cornea and to determine the refractive error. For example, the shape the cornea should have in the order for eye to be optically correct. Typically, a kerotograph image using a placido ring target such as described in U.S. Pat. No. 3,797,921 or in *Refractive Keratotomy, supra* is used. A topographic survey of the eye is made for comparison purposes and to provide the surgeon with the necessary information for correcting the refractive error. Once all of the preliminary information has been decided, the operation first proceeds by attaching the fixation ring 52 to the bottom of the adaptor sleeve 50. The adaptor sleeve nut 70 is then threaded into the sleeve 50 and is assembled so that the lower end 72 of the nut is withdrawn above the cornea 20. The fixation ring vacuum via conduit 54A is activated and adjusted sufficient to maintain the scleral fixation 52 stable upon the eye. The vacuum to the adaptor sleeve by way of conduit 54B is activated. Thereafter, sleeve 70 is rotated downwardly by the sleeve adjustment knob 76 in a clockwise direction. Rotation occurs in increments of 20 μm to place the beveled bottom 72 of the sleeve in close proximity of the cornea. Movement is slowly continued in increments until the bottom 72 touches the cornea. This will be immediately indicated by the establishment of vacuum pressure at the gauge on console 56. After the initial contact, the sleeve 70 is advanced further, e.g., about 40 μm to assure a good vacuum seal is established. The vacuum, by way of line 54B, is then released and the adaptor sleeve assembly is now positioned and ready for the next step.

The surgeon then by grasping the handle 150 places the micrometer assembly 80 into the top of the adaptor sleeve 70. The surgical knife 110 is then carefully placed into the bore of the micrometer assembly assuring that the blade surface does not contact any other surface in order to prevent inadvertent blade dulling. The micrometer nut 84 has been previously positioned to be at the top of its travel to assure that the blade is well above the cornea when inserted into the sleeve assembly. At this point the video imaging system is then inserted into the inner bore 114 of the surgical knife. the video camera 142 is designed to rest above the top of the surgical knife assembly. The video cable 144 is attached and inserted into the groove provided within the handle with the proximal end of the cable attached to the video monitor 145. At this point the vacuum is now applied once again via conduit 54B to the adaptor sleeve assembly. The surgical knife 110 is slowly moved by rotating the nut 84 in a clockwise direction as for example 40 μm at a time. In the preferred embodiment each individual marker line is 10 μm. As the knife nears the cornea, the corneal surface will come into clear view on the video monitor. Continued downward movement of the knife, for example, 20 μm increments is continued until the knife touches an approximate 2 mm area of corneal epithelium. This will establish the zero point of corneal touch. The surgical knife is then rotated a few cycles in order to define and identify the touch zone diameter as will be shown on the monitor. The depth of cut is determined accurately by the surgeon utilizing the Vernier scale. The micrometer nut 84 is then lowered the amount of cut which has been previously established by a pre-prepared refractive algorithm look-up table based upon touch zone diameter, targeted correction and the final optical zone. After the desired ablation depth has been "dialed in" by the micrometer assembly 80, the process is initiated. In one embodiment, the procedure is manual, and therefore, under the absolute control of the surgeon, with the process being visible at all times on the video monitor 145. A typical, but not limiting process, begins by rotation of the surgical knife in an oscillatory manner making one full revolution of the knife blade and then making a plurality, e.g., 5 oscillatory movements at a random rotational distance followed by a complete revolution in the opposite direction. This concept is continued at the completion of which the vacuum provided through conduit 54B is released and the micrometer assembly 80 removed from the sleeve. At this point the surgeon may use a surgical microscope which is swung into position over the adaptor sleeve assembly with connection being made to the video monitor to observe the treated optical zone. The vacuum, via conduit 54A, to the fixation ring is turned off and the fixation ring and adaptor ring assembly removed. The corneal surface is then scrubbed, treated and measured. If further correction is needed, the procedure is repeated.

What is claimed is:

1. A method of reprofiling a cornea, which comprises:

(a) performing a lamellar keratectomy to obtain a corneal lamella and reveal a stromal bed;

(b) scraping said stromal bed with a sharpened, substantially planar knife-edge blade to obtain a desired curvature, said knife-edge blade being oriented substantially perpendicular relative to said stromal bed; and (c) replacing said corneal lamella upon said stromal bed.

2. A method of reprofiling a cornea, which comprises:

(a) performing a lamellar keratectomy to obtain a corneal lamella and reveal a stromal bed;

(b) rotating or oscillating a scraping tool upon said stromal bed to modify the contour of said stromal bed and obtain a desired curvature, said scraping tool having at least one sharpened, substantially planar knife-edge scraper blade for placement substantially perpendicular relative to said stromal bed; and (c) replacing said corneal lamella upon said stromal bed.

3. A method of reprofiling a cornea, which comprises:

(a) performing a lamellar keratectomy to obtain a corneal lamella and reveal a stromal bed;

(b) reshaping said stromal bed by laser photoablation to obtain a modified stromal bed of a desired curvature;

(c) smoothing the surface of said modified stromal bed by rotating or oscillating a scraping tool upon said surface; and (d) replacing said corneal lamella upon said stromal bed.

4. A method of reprofiling a cornea, which comprises:

(a) resetting a portion of said cornea in a manner such that said resected portion remains hinged to said cornea at one point;

(b) folding said resected portion up and away from said cornea to reveal a stromal bed;

(c) reshaping said stromal bed by laser photoablation to obtain a modified stromal bed of a desired curvature;

(d) smoothing the surface of said modified stromal bed by rotating or oscillating a scraping tool upon said surface; and (e) folding said resected portion back over said modified stromal bed.

5. A method of smoothing an anterior or exposed stromal corneal surface that has been corrugated, rippled, roughened or hardened due to the performance of a corneal refractive procedure, which comprises rotating or oscillating a scraping tool upon said corrugated, rippled, roughened or hardened surface until said surface is smoothed, said scraping tool having at least one sharpened, substantially planar knife-edge scraper blade for placement substantially perpendicular relative to said surface.

6. A method of dislocating debris from an anterior or exposed stromal corneal surface that has been corrugated, rippled, roughened or hardened due to the performance of a corneal refractive procedure, which comprises the steps of rotating or oscillating a scraping tool upon said debris-containing surface until said debris is dislodged, said scraping tool having at least one sharpened, substantially planar knife-edge scraper blade for placement substantially perpendicular relative to said surface.

7. A method of reprofiling a cornea, which comprises:

(a) resecting a portion of said cornea in a manner such that said resected portion remains hinged to said cornea at one point;

(b) folding said resected portion up and away from said cornea to reveal a stromal bed;

(c) performing a corneal refractive procedure to obtain a modified stromal bed of a desired curvature;

(d) smoothing the surface of said modified stromal bed by rotating or oscillating a scraping tool upon said surface; and (e) folding said resected portion back over said modified stromal bed.

8. A method of enhancing the optical zone of a cornea, which comprises the steps of performing a corneal refractive procedure as a primary technique for reprofiling said cornea followed by performing a distinct secondary technique, said secondary technique comprising rotating or oscillating a scraping tool upon the surface of said cornea, said scraping tool having at least one sharpened, substantially planar knife-edge scraper blade for placement substantially perpendicular relative to said surface.

9. An improved method of reprofiling a cornea wherein a corneal refractive procedure is performed upon an anterior or exposed stromal corneal surface as a primary technique to alter the refractive characteristics of said cornea, said procedure producing a worked area upon said cornea, the improvement comprising performing a distinct secondary technique to smooth and enhance said worked area, said secondary technique comprising rotating or oscillating a scraping tool upon said worked area of said cornea, said scraping tool having at least one sharpened, substantially planar knife-edge scraper blade for placement substantially perpendicular relative to said worked area.

10. An apparatus for reprofiling the anterior or stromal corneal portion of an eye of animals (including humans), said eye having a visual axis, to change the corneal radius and thus correct refractive errors, to finish or fine tune the cornea following a refractive correction procedure, or to otherwise smooth or enhance the cornea following a refractive correction procedure, comprising:

a transparent, resilient vacuum ring for attachment to said cornea coaxially to said visual axis;

an adapter for attachment to said vacuum ring, said adapter having conduits for vacuum communication with said vacuum ring;

a rotatable sleeve having a central bore axially extending therethrough for threadable engagement with said adapter, said rotatable sleeve having a lower end for making sealed contact with said cornea;

means to provide an independently controllable vacuum to said vacuum ring and to the interior of said sleeve;

a micrometer assembly, said micrometer assembly having a lower piece for coaxial engagement with said central bore of said sleeve and a micrometer nut for affecting incremental vertical movement of said assembly coaxially relative to a visual axis of said cornea; said lower piece and said micrometer nut having a central bore axially extending therethrough; and a scraping tool having a cylindrical body with a central bore, said body adapted to be received within said central bores of said lower piece of said micrometer assembly and said micrometer nut, said scraping tool having, at its upper end, an enlarged grip which rests upon said micrometer nut, and at least one sharpened knife edge substantially planar blade at its bottom end for scraping said anterior or stromal corneal portion.

11. The apparatus of claim 10, wherein said lower piece of said micrometer assembly is threadably connected with said central bore of said sleeve.

12. The apparatus of claim 10, wherein said lower piece of said micrometer assembly is integrally joined to said sleeve such that said lower piece and said sleeve are one piece.

13. The apparatus according to claim 10, further comprising a means for viewing said cornea during reprofiling, said means being insertable into said central bore of said scraping tool.

14. The apparatus according to claim 13, wherein said means for viewing comprises a magnifying stem for use in conjunction with a surgical microscope.

15. The apparatus according to claim 13, wherein said means for viewing comprises an optical viewer having an elongated sleeve insertable into said central bore of said scrapping tool, a lens, a video camera, and means to connect said camera to a video monitor.

16. The apparatus according to claim 15, further comprising a hand held support for retaining said micrometer assembly and means affixed to said hand held support to provide a controllable light source adjacent said vacuum ring and sleeve assembly.

17. The apparatus of claim 15, further comprising means for duplicating manual-like motion to impart to said scraping tool a rotating or oscillating motion about a vertical axis that is substantially coaxial with said visual axis.

18. A method of reprofiling the anterior or stromal corneal portion of an eye of animals (including humans), said eye having a visual axis, to change the corneal radius and thus correct refractive errors, to finish or fine tune the cornea following a refractive correction procedure, or to otherwise smooth or enhance the cornea following a refractive correction procedure, comprising the steps of:

positioning a vacuum ring upon the cornea and coaxial to a visual axis of said cornea;

positioning an adapter upon said vacuum ring, said adapter having conduits for vacuum communication with said vacuum ring;

threadably engaging a rotatable sleeve having a central bore axially extending therethrough with said adapter, said rotatable sleeve having a lower end for making sealed contact with said cornea;

supplying a first vacuum to said ring, and a second vacuum to an interior of said sleeve;

positioning a micrometer assembly upon said sleeve, said micrometer assembly having a lower piece for coaxial engagement with said central bore of said sleeve and a micrometer nut for affecting incremental vertical movement of said assembly coaxially relative to a visual axis of said cornea, said lower piece and said micrometer nut having a central bore axially extending therethrough;

positioning, upon said micrometer nut and within said central bores of said lower piece and said micrometer assembly, a corneal scraping tool having a sharpened knife edge substantially planar blade such that said knife edge is perpendicular to said visual axis of said cornea; and turning said scraping tool to scrape said anterior or stromal corneal portion to obtain a desired change in curvature.

19. The method of claim 18, wherein said lower piece of said micrometer assembly is threadably connected with said central bore of said sleeve.

20. The method of claim 18, wherein said lower piece of said micrometer assembly is integrally joined to said sleeve such that said lower piece and said sleeve are fixedly joined together.

21. The method according to claim 18, further comprising a means for viewing said cornea during reprofiling, said means being insertable into said central bore of said scraping tool.

22. The method according to claim 21, wherein said means for viewing comprises a magnifying stem for use in conjunction with a surgical microscope.

23. The method according to claim 21, wherein said means for viewing comprises an optical viewer having an elongated sleeve insertable into said central bore of said scraping tool, a lens, a video camera, and means to connect said camera to a video monitor.

24. The method according to claim 23, further comprising a hand held support for retaining said micrometer assembly and means affixed to said hand held support to provide a controllable light source adjacent said vacuum ring and sleeve assembly.

25. The method of claim 18, further comprising means for duplicating manual-like motion to impart to said scraping tool a rotating or oscillating motion about a vertical axis that is substantially coaxial with said visual axis.

* * * * *